(12) United States Patent
Bolognia et al.

(10) Patent No.: US 10,712,197 B2
(45) Date of Patent: Jul. 14, 2020

(54) OPTICAL SENSOR PACKAGE

(71) Applicant: Analog Devices Global Unlimited Company, Hamilton (BM)

(72) Inventors: David Frank Bolognia, Charlestown, MA (US); Camille Louis Huin, Taipei (TW); Brian Hall, North Andover, MA (US)

(73) Assignee: Analog Devices Global Unlimited Company, Hamilton (BM)

( * ) Notice: Subject to any disclaimer, the term of this patent is extended or adjusted under 35 U.S.C. 154(b) by 121 days.

(21) Appl. No.: 15/868,899

(22) Filed: Jan. 11, 2018

(65) Prior Publication Data
US 2019/0212190 A1 Jul. 11, 2019

(51) Int. Cl.
*G01J 1/02* (2006.01)
*G01J 1/42* (2006.01)
*A61B 5/024* (2006.01)
*G01J 1/04* (2006.01)

(52) U.S. Cl.
CPC ........ *G01J 1/0271* (2013.01); *A61B 5/02438* (2013.01); *G01J 1/0209* (2013.01); *G01J 1/0407* (2013.01); *G01J 1/0488* (2013.01); *G01J 1/42* (2013.01); *G01J 2001/0257* (2013.01)

(58) Field of Classification Search
CPC .................................. G01J 1/0271; G01J 1/42
USPC ........................................................ 250/239
See application file for complete search history.

(56) References Cited

U.S. PATENT DOCUMENTS

| | | |
|---|---|---|
| 5,247,597 A | 9/1993 | Blacha et al. |
| 5,289,002 A | 2/1994 | Tarn |
| 5,340,420 A | 8/1994 | Ozimek et al. |
| 5,421,928 A | 6/1995 | Knecht et al. |
| 5,500,505 A | 3/1996 | Jones |
| 5,643,472 A | 7/1997 | Engelsberg et al. |
| 5,907,395 A | 5/1999 | Schulz et al. |
| 6,113,835 A | 9/2000 | Kato et al. |
| 6,335,224 B1 | 1/2002 | Peterson et al. |

(Continued)

FOREIGN PATENT DOCUMENTS

| | | |
|---|---|---|
| DE | 19909242 A1 | 8/2000 |
| EP | 1 276 142 A2 | 1/2003 |

(Continued)

OTHER PUBLICATIONS

Notice of Allowance dated Oct. 25, 2016 in U.S. Appl. No. 14/945,255, filed Nov. 11, 2015 in 14 pages.

(Continued)

*Primary Examiner* — Seung C Sohn
(74) *Attorney, Agent, or Firm* — Knobbe, Martens, Olson & Bear, LLP

(57) ABSTRACT

An optical device package is disclosed. The optical device package includes a substrate that passes light at an optical wavelength. The optical device package also includes an optical device assembly that is mounted to the substrate. The optical device assembly comprises an optical device die. The optical device die has a first surface that is mounted to and facing the substrate and a second surface that is opposite the first surface. The optical device package further includes a molding compound that is disposed at least partially over the second surface of the integrated device die.

20 Claims, 13 Drawing Sheets

(56) References Cited

U.S. PATENT DOCUMENTS

| | | | |
|---|---|---|---|
| 6,344,664 B1 | 2/2002 | Trezza et al. | |
| 6,352,880 B1 | 3/2002 | Takai et al. | |
| 6,379,988 B1 | 4/2002 | Peterson et al. | |
| 6,396,116 B1 | 5/2002 | Kelly et al. | |
| 6,489,670 B1* | 12/2002 | Peterson | B81B 7/0067 257/433 |
| 6,489,686 B2 | 12/2002 | Farooq et al. | |
| 6,531,328 B1 | 3/2003 | Chen | |
| 6,576,867 B1 | 6/2003 | Lu et al. | |
| 6,602,430 B1 | 8/2003 | Nally et al. | |
| 6,707,161 B2 | 3/2004 | Moon et al. | |
| 6,787,916 B2 | 9/2004 | Halahan | |
| 6,825,065 B2 | 11/2004 | Moon et al. | |
| 6,849,916 B1 | 2/2005 | Glenn et al. | |
| 6,861,641 B1 | 3/2005 | Adams | |
| 6,864,460 B2 | 3/2005 | Cummings et al. | |
| 6,869,231 B2 | 3/2005 | Chiu et al. | |
| 6,878,564 B2 | 4/2005 | Silverbrook | |
| 6,878,900 B2 | 4/2005 | Corkum et al. | |
| 6,915,049 B2 | 7/2005 | Murata | |
| 6,930,398 B1 | 8/2005 | Sun et al. | |
| 7,049,639 B2 | 5/2006 | Wang et al. | |
| 7,209,362 B2 | 4/2007 | Bando | |
| 7,279,343 B1 | 10/2007 | Weaver et al. | |
| 7,294,827 B2 | 11/2007 | Tan et al. | |
| 7,335,922 B2 | 2/2008 | Plaine et al. | |
| 7,348,203 B2 | 3/2008 | Kaushal et al. | |
| 7,405,487 B2 | 7/2008 | Brand | |
| 7,442,559 B2 | 10/2008 | Auburger et al. | |
| 7,485,848 B2 | 2/2009 | Minamio | |
| 7,720,337 B2 | 5/2010 | Lu et al. | |
| 7,723,146 B2 | 5/2010 | Chow et al. | |
| 7,755,030 B2 | 7/2010 | Minamio | |
| 7,777,172 B2 | 8/2010 | Hernoult | |
| 7,786,186 B2 | 8/2010 | Patterson | |
| 7,807,505 B2 | 10/2010 | Farnworth et al. | |
| 7,812,416 B2 | 10/2010 | Courcimault | |
| 7,838,899 B2 | 11/2010 | Chow et al. | |
| 7,858,437 B2 | 12/2010 | Jung et al. | |
| 8,033,446 B2 | 10/2011 | Wada et al. | |
| 8,115,307 B2 | 2/2012 | Toyama et al. | |
| 8,378,502 B2 | 2/2013 | Chow et al. | |
| 8,399,994 B2 | 3/2013 | Roh et al. | |
| 8,466,902 B2 | 6/2013 | Boer et al. | |
| 8,531,018 B2 | 9/2013 | Pahl | |
| 8,538,215 B2 | 9/2013 | Deliwala et al. | |
| 8,601,677 B2 | 12/2013 | Doanyb et al. | |
| 8,604,436 B1 | 12/2013 | Patel et al. | |
| 8,766,186 B2 | 7/2014 | Kierse et al. | |
| 8,779,361 B2 | 7/2014 | Costello et al. | |
| 8,822,925 B1 | 9/2014 | Patel et al. | |
| 8,920,332 B2 | 12/2014 | Hong et al. | |
| 8,933,386 B2 | 1/2015 | Kamamori et al. | |
| 8,946,664 B2 | 2/2015 | Tsukagoshi et al. | |
| 8,975,108 B2 | 3/2015 | Rudmann et al. | |
| 9,029,968 B2 | 5/2015 | Tsukagoshi et al. | |
| 9,731,959 B2* | 8/2017 | Sengupta | B81B 7/0048 |
| 9,960,328 B2* | 5/2018 | Clark | H01L 33/44 |
| 10,025,047 B1* | 7/2018 | Liu | H01L 25/167 |
| 2002/0021874 A1 | 2/2002 | Giboney et al. | |
| 2002/0181882 A1 | 12/2002 | Hibbs-Brenner et al. | |
| 2003/0197292 A1 | 10/2003 | Huang | |
| 2003/0219217 A1 | 11/2003 | Wickman et al. | |
| 2004/0037507 A1 | 2/2004 | Marion et al. | |
| 2005/0087522 A1 | 4/2005 | Sun et al. | |
| 2005/0135071 A1 | 6/2005 | Wang et al. | |
| 2005/0226569 A1 | 10/2005 | Sashinaka et al. | |
| 2006/0001116 A1 | 1/2006 | Auburger et al. | |
| 2006/0027479 A1 | 2/2006 | Auburger et al. | |
| 2006/0045421 A1 | 3/2006 | Baets et al. | |
| 2006/0049548 A1 | 3/2006 | Auburger et al. | |
| 2006/0126331 A1 | 6/2006 | Chien | |
| 2007/0222041 A1 | 9/2007 | Weng et al. | |
| 2007/0284549 A1 | 12/2007 | Mizuo et al. | |
| 2007/0291490 A1 | 12/2007 | Tajul et al. | |
| 2008/0074401 A1 | 3/2008 | Chung et al. | |
| 2008/0079019 A1 | 4/2008 | Huang et al. | |
| 2008/0157252 A1 | 7/2008 | Cheng et al. | |
| 2009/0011522 A1 | 1/2009 | Drennan et al. | |
| 2009/0014857 A1 | 1/2009 | Hufgard | |
| 2009/0046144 A1 | 2/2009 | Tuttle | |
| 2009/0070727 A1 | 3/2009 | Solomon | |
| 2009/0075092 A1 | 3/2009 | Varaprasad | |
| 2009/0134481 A1 | 5/2009 | Sengupta | |
| 2009/0189177 A1 | 7/2009 | Lee et al. | |
| 2009/0213262 A1 | 8/2009 | Singh et al. | |
| 2009/0218588 A1 | 9/2009 | Panaccione et al. | |
| 2009/0226130 A1 | 9/2009 | Doany et al. | |
| 2009/0269006 A1 | 10/2009 | Ishikawa et al. | |
| 2010/0019393 A1 | 1/2010 | Hsieh et al. | |
| 2010/0187557 A1 | 7/2010 | Samoilov et al. | |
| 2010/0200998 A1 | 8/2010 | Furuta et al. | |
| 2010/0244217 A1 | 9/2010 | Ha et al. | |
| 2010/0259766 A1 | 10/2010 | Wiese et al. | |
| 2010/0327164 A1 | 12/2010 | Costello et al. | |
| 2011/0024899 A1 | 2/2011 | Masumoto et al. | |
| 2011/0062572 A1 | 3/2011 | Steijer et al. | |
| 2011/0176765 A1 | 7/2011 | Lee | |
| 2011/0204233 A1 | 8/2011 | Costello et al. | |
| 2011/0254763 A1 | 10/2011 | Lee et al. | |
| 2012/0027234 A1 | 2/2012 | Goida | |
| 2012/0287443 A1 | 11/2012 | Lin et al. | |
| 2012/0313204 A1 | 12/2012 | Haddad et al. | |
| 2013/0012276 A1 | 1/2013 | Coffy et al. | |
| 2013/0032388 A1 | 2/2013 | Lin et al. | |
| 2013/0082951 A1 | 4/2013 | Tanaka et al. | |
| 2013/0147727 A1 | 6/2013 | Lee et al. | |
| 2013/0230273 A1 | 9/2013 | Doscher et al. | |
| 2013/0285185 A1 | 10/2013 | Park et al. | |
| 2013/0292706 A1 | 11/2013 | Costello et al. | |
| 2013/0292786 A1 | 11/2013 | Sengupta | |
| 2013/0327931 A1 | 12/2013 | Hsu et al. | |
| 2014/0027867 A1 | 1/2014 | Goida et al. | |
| 2014/0340302 A1 | 11/2014 | Sengupta et al. | |
| 2015/0187608 A1* | 7/2015 | Ganesan | H01L 23/49811 257/738 |
| 2015/0270305 A1 | 9/2015 | Hayashi et al. | |
| 2015/0378013 A1 | 12/2015 | Bikumandla et al. | |
| 2016/0013223 A1 | 1/2016 | Chang et al. | |
| 2016/0068387 A1* | 3/2016 | Nakanishi | B81C 1/0023 257/415 |
| 2016/0124166 A1* | 5/2016 | Braunisch | G02B 6/12 156/60 |
| 2016/0276503 A1 | 9/2016 | Kasano | |

FOREIGN PATENT DOCUMENTS

| | | |
|---|---|---|
| WO | WO 2001/068460 A2 | 9/2001 |
| WO | WO 2007/005636 A2 | 1/2007 |

OTHER PUBLICATIONS

Office Action dated Aug. 8, 2016 in U.S. Appl. No. 14/276,238, filed May 13, 2014, in 27 pages.

Office Action dated Jun. 17, 2014 in U.S. Appl. No. 13/560,855, filed Jul. 27, 2012 in 11 pages.

Office Action dated Sep. 3, 2014 in U.S. Appl. No. 13/462,604, filed May 2, 2012 in 15 pages.

Office Action dated Jun. 19, 2015 in U.S. Appl. No. 13/462,604, filed May 2, 2012 in 15 pages.

* cited by examiner

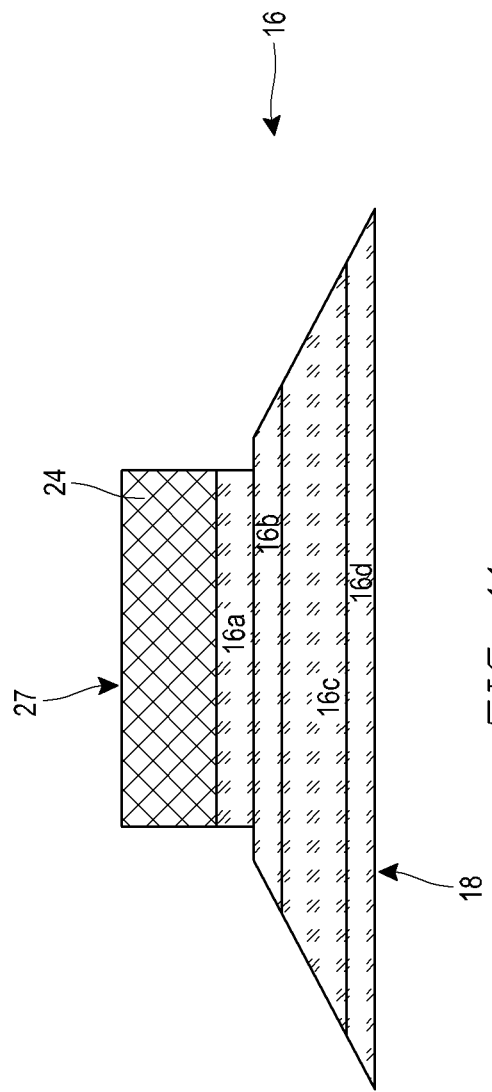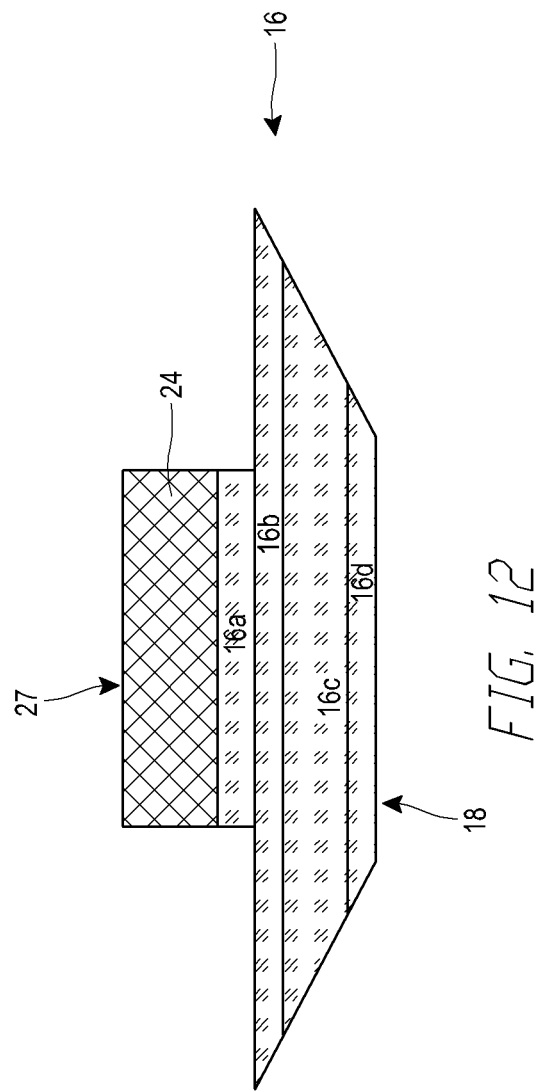

OPTICAL SENSOR PACKAGE

BACKGROUND

Field

The field relates to a sensor package and more particularly, to a sensor package with a transparent substrate.

Description of the Related Art

Optical sensors are used widely in various fields such as consumer electronics, healthcare, and telecommunications. For example, optical sensors can be used to detect and measure, for example, heart rate. Some optical sensors can be wearable, for example, as a wristband, watch or armband, in which the optical sensor and detector are positioned so as to face the user's body to detect optical signals representative of the user's biological signatures (e.g., heart rate, etc.). An optical sensor system can include various components, such as an optical emitter, an optical sensor die, and an application-specific integrated circuit (ASIC). The ASIC may be configured to process the output signal from the optical sensor die.

Optical device dies such as optical sensors and optical emitters are typically mounted on a package substrate (such as a printed circuit board) and covered by an optically transparent material. Many conventional optical device dies are relatively thick, which may be undesirable for a user to wear and/or may degrade optical sensitivity. Thus, there remains a need for improved optical sensors.

SUMMARY

The innovations described in the claims each have several features, no single one of which is solely responsible for its desirable attributes. Without limiting the scope of the claims, some prominent features of this disclosure will now be briefly described.

In one aspect, an optical device package is disclosed. The optical device package includes a substrate that passes light at an optical wavelength. The optical device package also includes an optical device assembly mounted to the substrate. The optical device assembly comprises an integrated device die. The integrated device die has a first surface mounted to and facing the substrate and a second surface opposite the first surface. The optical device package further includes a molding compound disposed at least partially over the second surface of the integrated device die.

In one aspect, an optical device package is disclosed. The optical device package includes a substrate that passes light at an optical wavelength. The optical device package can also include an optical device die having a first surface mounted to the substrate. The optical device die is configured to transmit or detect light through the substrate at the optical wavelength. The optical device package further includes a processor die mounted to the substrate. The processor die is electrically connected to the optical device die.

In one aspect, an optical device package is disclosed. The optical device package includes a substrate that passes light at an optical wavelength. The substrate has a first side, a second side that is opposite the first side and a side wall that extends between the first and second sides. The optical device package also includes an optical device die that has a first surface mounted to and facing the second side of the substrate. The optical device die is configured to transmit or detect light through the substrate. The optical device package further includes a frame that is disposed at least partially around the side wall and at least partially over a back side of the optical device die. The frame is opaque to at least the optical wavelength.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

Specific implementations of the invention will now be described with reference to the following drawings, which are provided by way of example, and not limitation.

FIG. 11 shows a schematic cross-sectional view of a sensor die attached to the substrate, according to various embodiments.

FIG. 12 shows a schematic cross-sectional view of a sensor die attached to the substrate and having a different shape from the substrate in FIG. 11, according to various embodiments.

DETAILED DESCRIPTION

Figure 1:
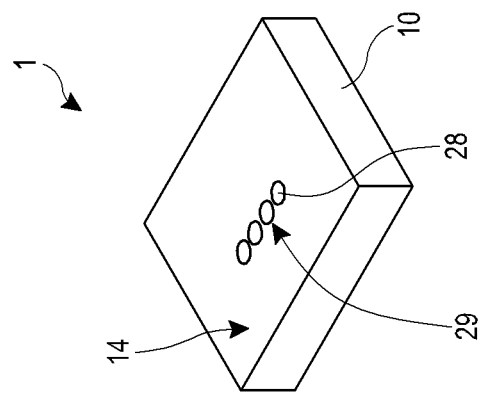
FIG. 1 is a schematic isometric view of a sensor package having a first die (not shown) embedded in a frame with its front side facing upwardly.

The following detail description of certain embodiments presents various descriptions of specific embodiments.

However, the disclosed embodiments can be embodied in myriad different ways as defined and covered by the claims. In this description, reference is made to the drawings in which like reference numerals indicate identical or functionally similar elements.

Various embodiments disclosed herein relate to optical sensors that have a compact or low profile. For example, various optical sensors disclosed herein can be configured for use in vital signs monitoring (VSM) sensor systems (e.g., heart rate monitoring systems, blood pressure monitoring systems, blood quality monitoring systems, muscle monitoring systems, bone density measuring systems etc.) for humans and animals. The embodiments disclosed herein may be particularly beneficial for use with wearable VSM sensor systems. Wearable VSM sensor systems can include sensor systems associated with wearable items such as, for example, wristbands, armbands, watches, eye glasses, ear rings, clothes (e.g., belts, t-shorts, bras, socks, swim suits, etc.). The embodiments disclosed herein may also be beneficial for use with non-wearable sensor systems. Non-wearable sensor systems can include sensor systems associated with devices such as, for example, fitness equipment (e.g., treadmills, bicycles, exercise bikes, etc.), cell phones, and automobiles.

A heart rate can be measured electronically by detecting heart beats/pulses and counting the pulses for a range of time to calculate pulses per minute. In some types, heart rate monitoring systems utilizing optical sensors, known as photoplethysmography (PPG), can implement the same or similar steps. To detect the heart pulse, light is emitted from an optical emitter, for example a light emitting diode (LED), towards a part of a user body. The emitted light is reflected and/or scattered from the body, and the intensity of the reflected and/or scattered light is detected by an optical sensor die, which can comprise a photodiode array (PDA). Some wavelengths of the light emitted from the optical emitter can penetrate through the skin of the user's body, and light reflected from within the user's body can be representative of a blood flow, a heartbeat, and/or a blood pressure in the user's body. By detecting changes in light intensity (representative of blood flow in the user), a processor die, e.g., an application-specific integrated circuit (ASIC), can process collected data, for example, by counting the pulses per minute and/or amplifying the data for display to the user.

An optical sensor package can include an optical sensor die, an optical emitter die, and a processor die (e.g., an ASIC) mounted on a substrate such as printed circuit board (PCB), and the components can be covered by a cover glass. In such packages, light emitted from the optical emitter die can pass through the glass cover to reach the target object (e.g., a blood vessel, muscle tissue, etc.), and the reflected and/or scattered light from the object can pass through the glass cover to reach the optical sensor die. Conventional structures often have a space between the glass cover (lid) and the optical device dies to reduce stress on the optical device dies and/or ensure consistent optical behaviour from device to device. However, the space can negatively affect optical performance of the system because the optical device dies are farther from the target object than in arrangements without the space which can cause, for example, degradation of optical signal by ambient light. In some embodiments, this is at least partly because, a distance between the optical device die and the target object and a light intensity are related. For example, the intensity and the distance can be related by the inverse-square law. In a heart rate monitoring system, back scattered light from blood vessels is detected and reflected light from other parts of the body (e.g., fat, skin, muscle, etc.) may be unwanted. In some embodiments, the spacing between the blood vessels and the optical dies can allow for the back scattered light from the blood vessels to be detected and the reflected light from other parts of the body to miss the optical sensor die. Further, the space adds a thickness to a dimension of the optical sensor perpendicular to a glass surface that faces the user body. Moreover, the presence of both a package substrate (such as a PCB) and a cover glass contribute to the overall thickness of the package. Accordingly, it can be desirable to provide an optical sensor package that increases optical performance and/or reduces the thickness of the package.

Figure 2:
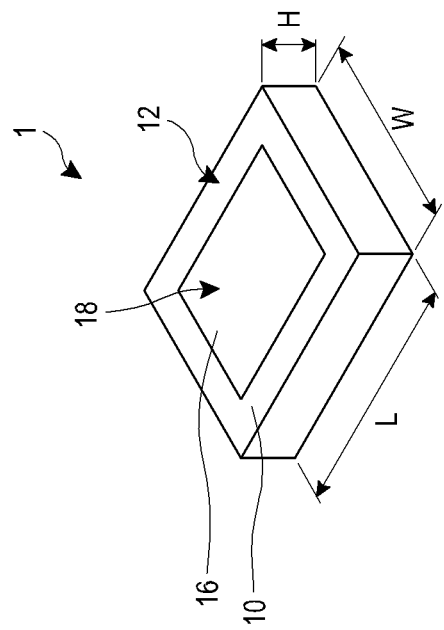
FIG. 2 is a schematic isometric view of the sensor package of FIG. 1 with its back side facing upwardly.
Figure 3:
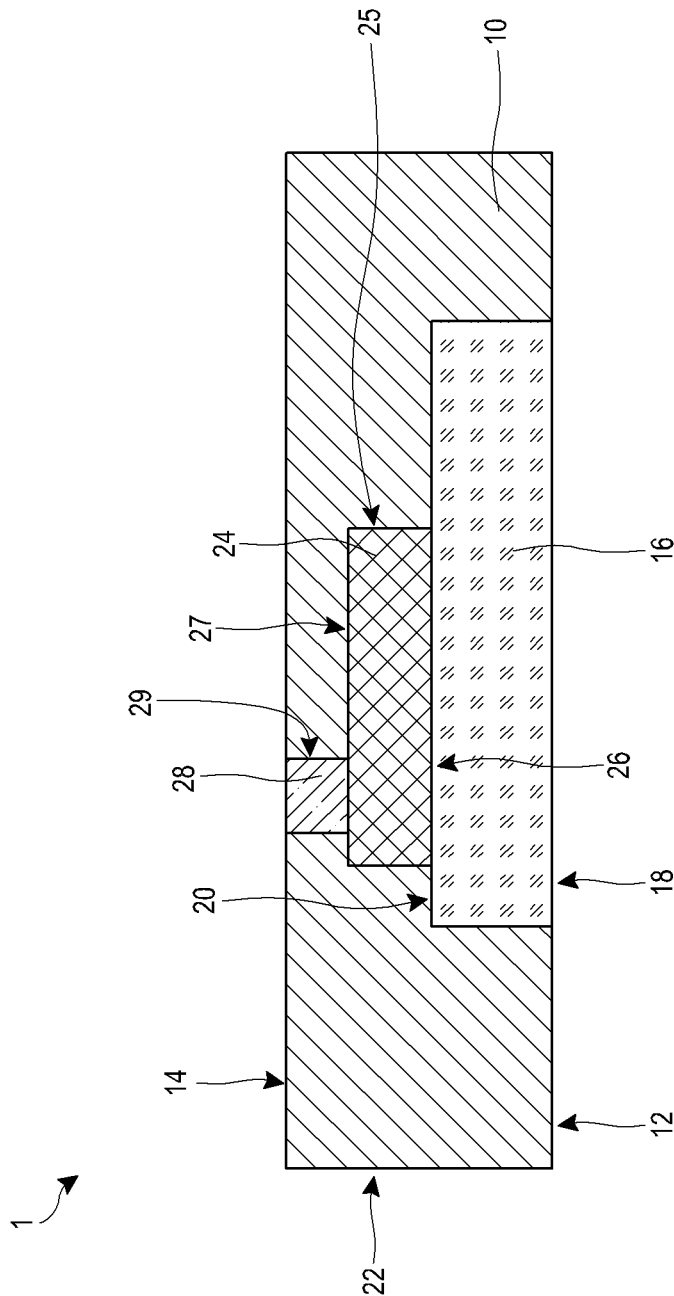
FIG. 3 is a cross sectional side view of the sensor package of FIGS. 1 and 2.
Figure 4:
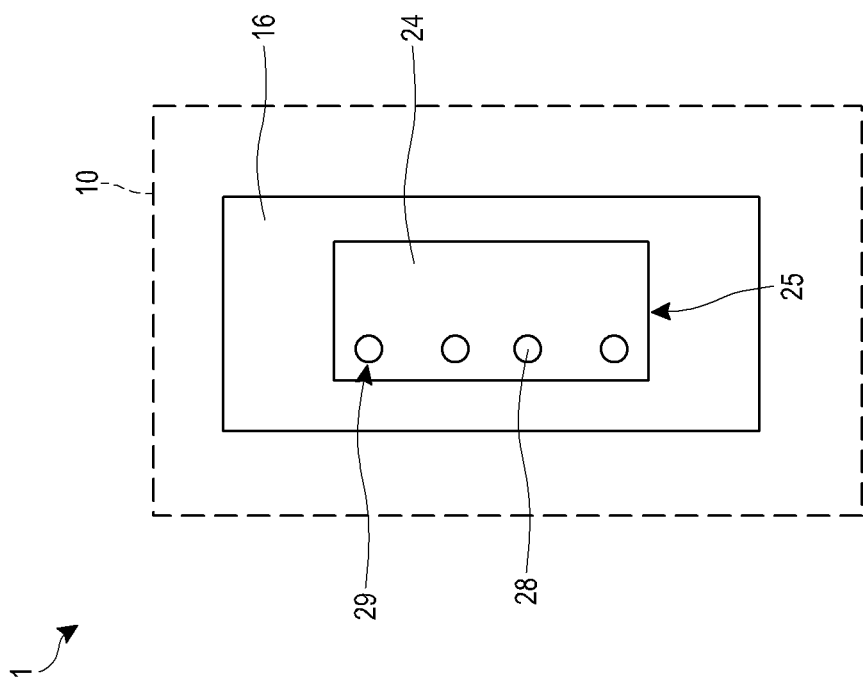
FIG. 4 is a schematic top plan view of the package of FIGS. 1-3 with the frame hidden to show components embedded in the frame.

FIG. 1 is a schematic isometric view of a sensor package 1 having a first die (not shown) disposed in a frame 10 with its front side 12 facing upwardly. FIG. 2 shows the sensor package 1 of FIG. 1 with its back side 14 opposite the front side 12 facing upwardly. FIG. 3 is a schematic cross-sectional side view of the sensor package 1 of FIGS. 1 and 2. FIG. 4 is a top plan view of the package 1 with the frame 10 hidden to show components disposed in the frame 10. The first die illustrated in FIGS. 1-4 comprises an optical device die in the form of a sensor die 24. However, it should be understood that the optical device die can comprise an optical emitter die, in some embodiments. As explained below, in some embodiments, the sensor and emitter dies can be provided in the same package. In other embodiments, the sensor die can be provided in a separate package from the emitter die. In the illustrated embodiment, during operation, a first side 18 of a substrate 16, on the front side 12 of the package 1, can receive light reflected and/or scattered from a target surface (e.g., skin from a user). As explained herein, the substrate 16 can be transparent to at least some wavelengths of light emitted by an emitter die (not shown). The light reflected and/or scattered from the target surface can pass through the transparent substrate 16 to impinge on a front sensor surface 26 of the sensor die 24. As shown in FIG. 3, the front sensor surface 26 can face and be mounted to the transparent substrate 16. In the illustrated embodiment, the front sensor surface 26 can comprise an active surface of the sensor die 24. For example, one or more photosensitive detector elements (e.g., a photodiode array, or PDA) can be provided at or near the front sensor surface 26. The detected light can be converted to electrical signal(s) by circuitry in the sensor die 24, and the electrical signal(s) can be transferred via one or more electrical interconnect(s) 28 on a back sensor surface 27 of the sensor die 24 to an external structure, such as a packaging substrate or a motherboard. It should be understood that an active surface of the sensor die 24 can be at or near the front sensor surface 26, at or near the back sensor surface 27, and/or can be accessed from the back surface.

The substrate 16 can comprise any optically transparent material (e.g., a glass substrate) for passing light at a range of wavelengths, e.g., at a range that includes at least some wavelengths emitted by an associated emitter die. The range may vary depending on the wavelengths emitted by the associated emitter die and/or by the target objects to be monitored. Thus, in the embodiments disclosed herein, the substrate 16 can be generally transparent to light at wavelengths which are sensed or detected by the sensor die and/or emitted by the emitter die. In some embodiments, the substrate can comprise a coating. For example, the coating can be applied at a portion of the substrate 16 to block certain range(s) of wavelengths that can be detected by the sensor die 24 and/or that can pass through the transparent material. For example, when green light (e.g., light with 492 nm to 577 nm wavelengths) is the light of interest, the coating may block or attenuate light other than green light that can be detected by the sensor die 24 and/or that can pass through the transparent material. In some embodiments, the substrate 16 can comprise a prism. In such embodiments, the prism may spread incoming light into different colors or wavelengths. By disposing the sensor die 24 at a location on the substrate 16, the sensor die 24 may detect the range(s) of wavelengths. For example, when green light (e.g., light with 492 nm to 577 nm wavelengths) is the light of interest, sensor die 24 can be disposed at a location on the substrate 16 where only the green light is passed. In some embodiments, a plurality of sensors can be disposed on different locations of the substrate 16 to detect different ranges of wavelengths. As shown in FIG. 3, the substrate 16 has a first side 18 and a second side 20 with the first side 18 being exposed at the front side 12 of the package 1. In a system, such as a heart rate monitoring system, the first side 18 of the substrate 16 can make physical contact with a user's skin during use of the package 1, in various embodiments. In some embodiments, the substrate 16 can have multiple layers of optically transparent materials, as explained below in relation to FIGS. 11 and 12. As explained herein, for example, one or more layers of the substrate 16 can comprise a filter, diffuser, splitter, polarizer, waveguide, and/or a beam steering element. The substrate 16 can form any suitable shape for its designed purposes. Embodiments disclosed herein can have the transparent substrate 16 both as a base for mounting the sensor die 24 (and/or emitter die) and as a cover or window providing a light path for the sensor die 24. Such embodiments may beneficially reduce a package height H of the package 1, as compared to embodiments having a separate substrate and a separate cover.

In some embodiments, the frame 10 can be optically opaque to block unwanted light (including ambient light) from reaching the front sensor surface 26 of the sensor die 24, e.g., to prevent interference with the light representative of the signal to be measured (e.g., the light reflected and/or transmitted from the target surface). For example, the frame 10 can comprise a material that is opaque or blocks electromagnetic spectrum or light at wavelengths in a range of 1 nm to 1 mm. The frame 10 can comprise a molding compound (e.g., epoxy resin) that is molded over portions of the back surface 20 of the substrate 16, the back sensor surface 27 and side surfaces 25 of the sensor die 24, and lateral sides of the electrical interconnects 28. The frame 10 can have any suitable shape. For example, a side wall 22 of the frame 10 can be angled to fit in various types of electronic devices (e.g. within a cavity of a wearable device, such as a smart watch or fitness monitor). The frame 10 can comprise a multi-layered frame in which two or more different molding compounds or other materials define the frame 10. Further, a cover can be provided that surrounds the frame 10 for providing additional light blocking, for providing physical protection and/or for design purposes. In some embodiments, the frame 10 can include a magnetic material for attaching the package 1 to an external device. In such embodiments, an insulator may be applied over the magnetic material. In some embodiments, the magnetic material can be disposed as the molding compound or as a solid magnet embedded in the molding compound.

In some embodiments, the electrical interconnects 28, as shown in FIGS. 2 and 3, can be connected to an external device using, for example, solder balls. In FIGS. 2 and 4, four electrical interconnects 28 are illustrated on the back side 14 of the package 1. However, any suitable number of electrical interconnects 28 can be disposed. In the illustrated embodiment, one or more through mold vias (TMVs) 29 can extend from the back surface 27 of the sensor die 24 to the back side 14 of the frame 10, such that the interconnects 28 are exposed at the back side 14 of the frame 10. The electrical interconnects 28 can extend from corresponding bond pads on the back surface 27 of the sensor die 24 through the TMVs 29 to the back side 14 of the frame 10. In some embodiments, the TMVs 29 can be formed after the frame 10 is disposed over the sensor die 24. In such embodiments, the TMVs 29 can be formed after disposition of the frame 10 by removing portions of the frame 10 (e.g., etching, drilling, laser drilling, strip gringing etc.). In some other embodiments, the electrical interconnects 28 can be disposed on the back sensor surface 27 prior to disposing the frame 10 over the sensor die 24, thereby forming the TMVs 29 when the frame 10 is disposed about the interconnects 28 (e.g., the molding compound of the frame 10 can be molded about the interconnects 28. Having the electrical interconnects 28 in the TMVs 29 to electrically connect the sensor die 24 to an external device can be beneficial. For example, in some embodiments, the electrical interconnects 28 can provide a relatively short electrical pathway for an electrical connection between the sensor die 24 and the external device, which may reduce the package height H of the package 1, compared to other attachment methods. In some embodiment, the relatively short electrical pathway can reduce electrical parasitic (e.g., parasitic inductance, parasitic capacitance, parasitic resistance, etc.). Further, having the electrical interconnects 28 in the TMVs 29 to electrically connect the sensor die 24 to an external device may also improve thermal performances of components in the package 1. In some embodiments, the electrical interconnects 28 can include horizontal traces and vertical vias.

Referring to FIG. 1, the package 1 has a package length L, a package width W, and the package height H. An area that is defined by the package length L and the package width W of the package 1 illustrated in FIG. 1 can be, for example, in a range of 0.1 mm$^2$ to 2 cm$^2$, in a range of 1 mm$^2$ to 40 mm$^2$, in a range of 10 mm$^2$ to 30 mm$^2$, or in a range of 15 mm$^2$ to 20 mm$^2$. In some embodiments, the size of the area can depend on the intensity of the reflected light to be detected by the sensor die 24. For example, the package 1 can have a relatively small area when the reflected light has a relatively high intensity and the package 1 can have a relatively large area when the reflected light has a relatively low intensity. The package height H of the package 1 shown in FIG. 1 can be, for example, in a range of 0.3 mm to 1.2 mm, or in a range of 0.7 mm to 1 mm.

Figure 5:
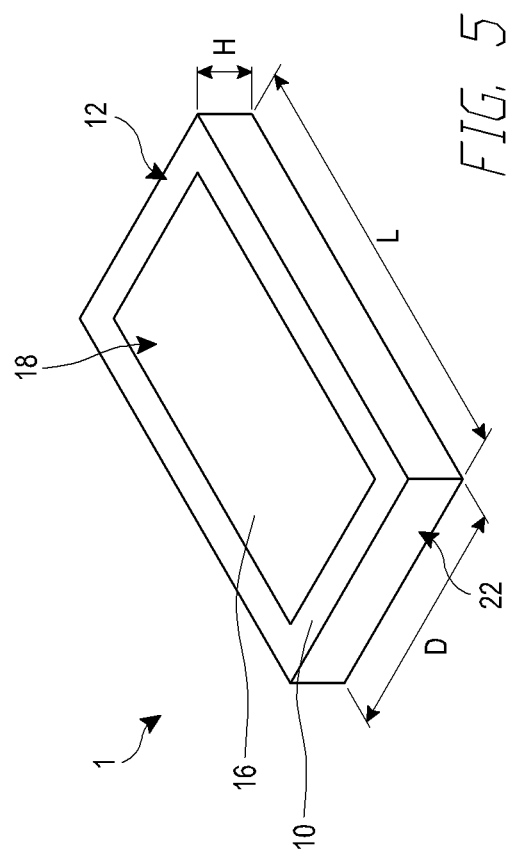
FIG. 5 is a schematic isometric view of a sensor package having a sensor die, an emitter die, and an integrated device die (not shown) embedded in a frame with its front side facing upwardly.
Figure 6:
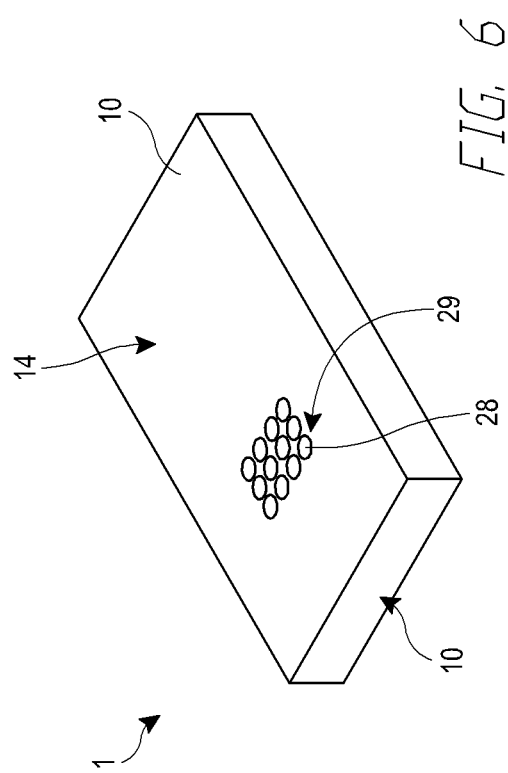
FIG. 6 is a schematic isometric view of the sensor package of FIG. 5 with its back side facing upwardly.
Figure 7:
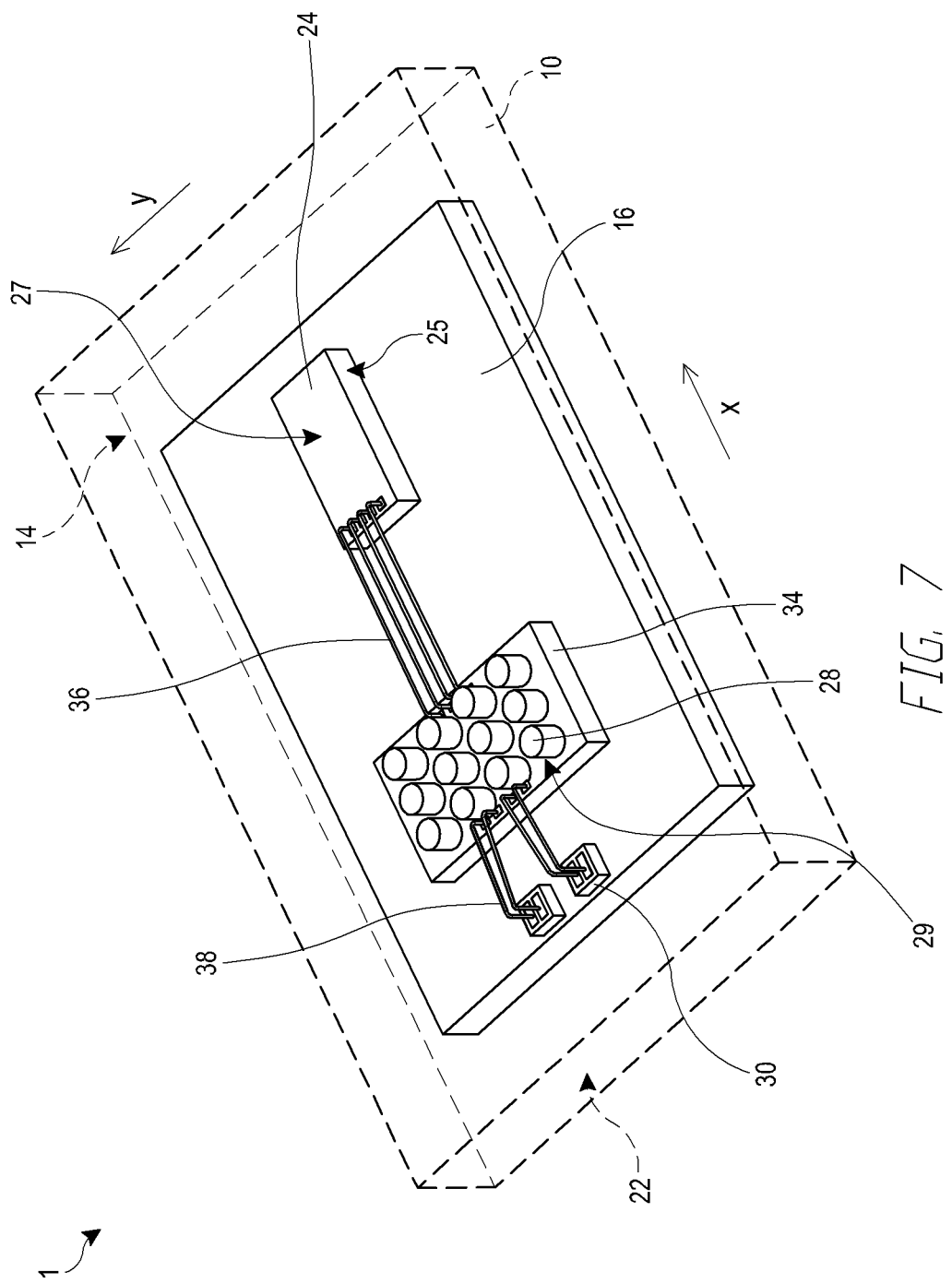
FIG. 7 is a schematic isometric view of the package in an embodiment with the frame hidden to show components embedded in the frame.
Figure 8:
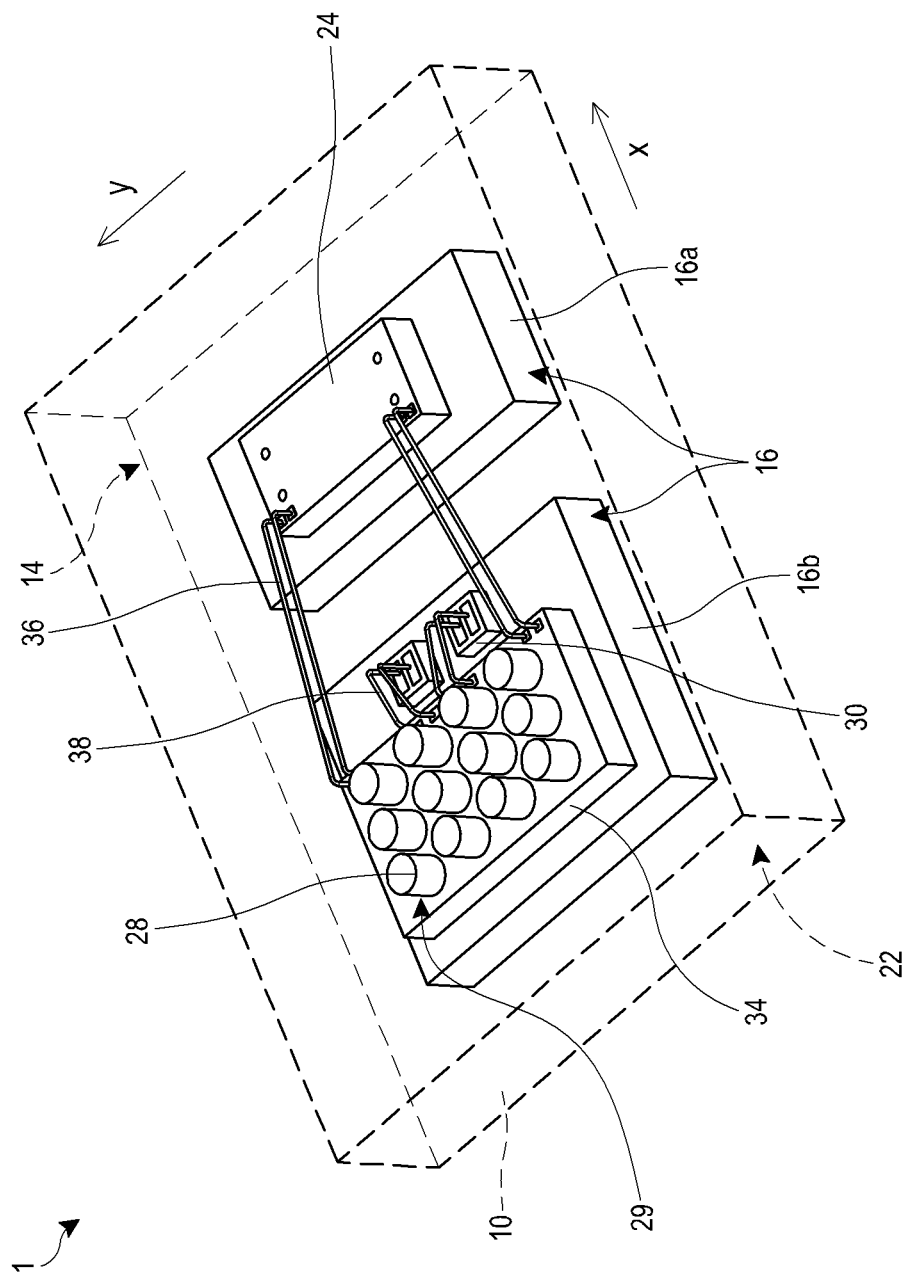
FIG. 8 is a schematic isometric view of the package in an embodiment with the frame hidden to show components embedded in the frame.
Figure 9:
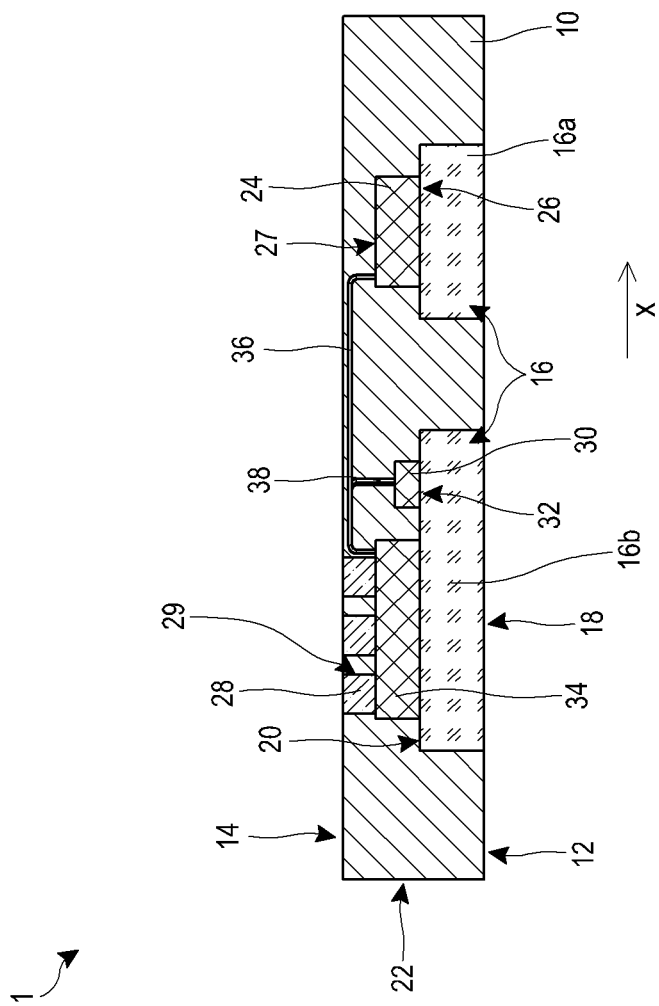
FIG. 9 is a schematic cross-sectional side view of the sensor package of FIG. 8.
Figure 10:
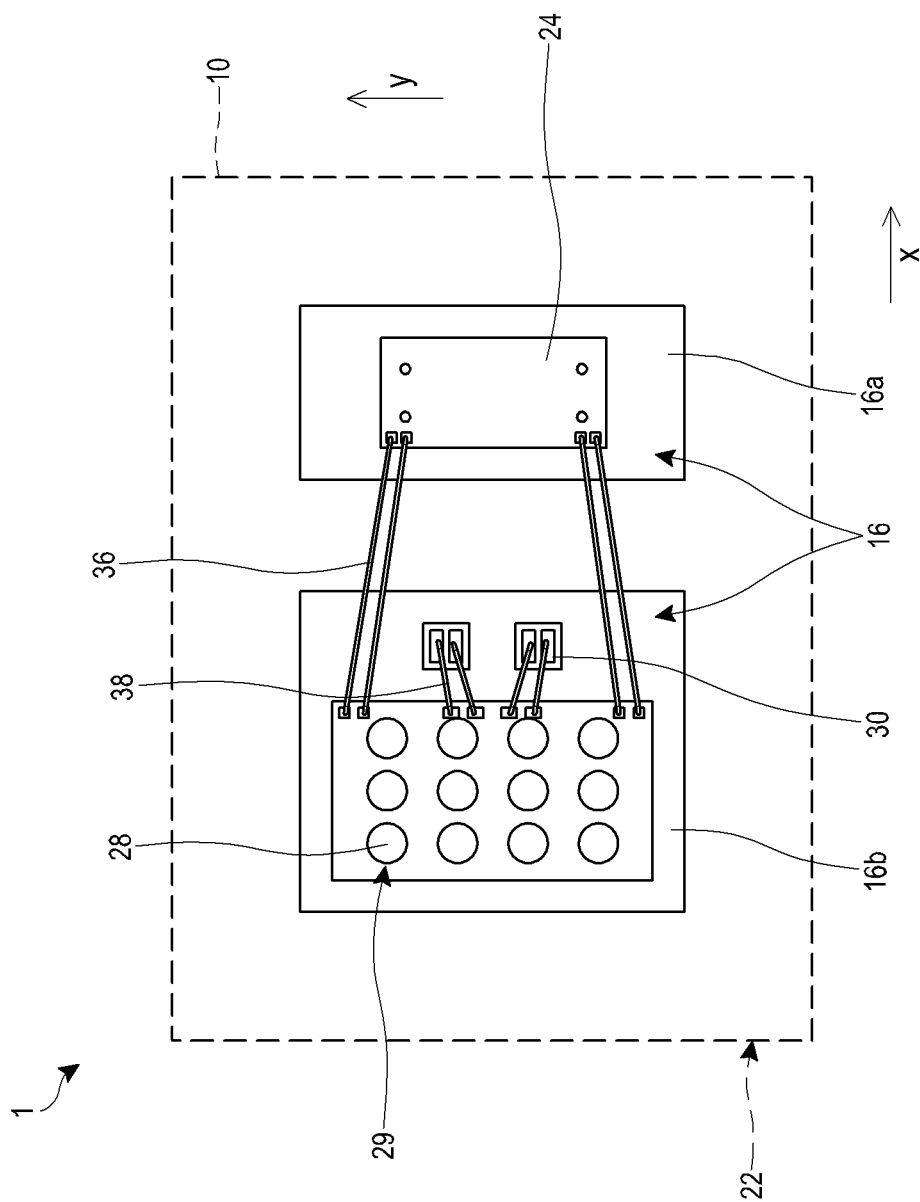
FIG. 10 is a schematic top plan view of the package of FIGS. 8 and 9 with the frame hidden to show components embedded in the frame.

FIGS. 5-9 show other embodiments of the sensor package 1 in various views. Unless otherwise noted, components of FIGS. 5-9 are the same as or generally similar to like-numbered components shown in FIGS. 1-4. FIGS. 5-9 show the sensor package 1 having a sensor die 24, emitter dies 30, and an integrated device die 34 embedded in a frame 10. In FIG. 5 the front side 12 of the sensor package faces upwardly. In FIG. 6 the back side 14 of the sensor package 1 faces upwardly. FIG. 7 is a top perspective view of the package 1 in one embodiment with the frame 10 hidden to show components embedded in the frame 10. FIG. 8 is a top perspective view of the package 1 in another embodiment with the frame 10 hidden to show components embedded in the frame 10. FIG. 9 is a cross-sectional side view of the sensor package 1 of FIG. 8. FIG. 10 is a top plan view of the package 1 of FIGS. 8 and 9 with the frame 10 hidden to show components embedded in the frame 10.

The embodiment shown in FIG. 7 has a substrate 16 for carrying the sensor die 24, the emitter dies 30, and the integrated device die 34 (such as an ASIC for controlling the emitter dies 30 and/or processing signals from the sensor die 24). The sensor die 24, the emitter dies 30, and the integrated device die 34 can each have bond pads to provide electrical communication therebetween. The sensor die 24, the emitter dies 30, and the integrated device die 34 can be electrically connected by way of wire bonding via wires 36, 38 at the bond pads. In alternative embodiments, there can be traces on the surface of or embedded in the substrate 16 to electrically connect the sensor die 24, the emitter dies 30, and the integrated device die 34.

The integrated device die 34 can send a signal to the emitter dies 30 and/or receive sensed data from the sensor die 24 for processing the sensed data, including, e.g., pre-processing the sensed data by way of analog-to-digital conversion, etc. The processed data can be transferred to an external device via the electrical interconnects 28. For example, the integrated device die 34 can send a signal to the emitter die 30 to cause the emitter die 30 to emit light and receive the data from the sensor die 24 to amplify data signals, pre-process or convert data signals, and/or calculate pulse per minute.

The sensor die 24, the emitter dies 30, and the integrated device die 34 illustrated in FIG. 7 are disposed along a longitudinal axis x of the package 1, where the device die 34 is disposed between the sensor die 24 and the emitter dies 30. This arrangement can be advantageous in minimizing direct sensing of light from the emitter dies 30 within the package 1. However, other embodiments can have any other arrangements of these components. For example, the sensor die 24 can be disposed in between the device die 34 and the emitter die 30. For another example, the sensor die 24 and the emitter die 30 can be disposed next to each other along a transverse axis y, transverse to the longitudinal axis x, and the sensor die 24 and the device die 34 can be disposed next to each other along the longitudinal axis x.

The sensor die 24, the emitter die 30, and the integrated device die 34 can be oriented in any orientation suitable. The sensor die 24 illustrated in FIG. 7 has its longer edge along the longitudinal axis x. However, the sensor die 24 can be oriented 90° from such orientation to have its longer edge along the transverse axis y (see for example, FIG. 8). It should be understood, however, that the sensor die 24 can have any suitable shape.

FIGS. 8-10 shows another embodiment of the package 1. In FIGS. 8-10, the substrate 16 comprises first and second substrate sections 16a, 16b spaced apart from each other, each of which can comprise a transparent (e.g., glass) substrate. The sensor die 24 is mounted to the first substrate sections 16a, and the emitter die 30 and the device die 34 is mounted to the second substrate section 16b. The first and second substrate sections 16a, 16b can be spaced by a portion of the frame 10 (e.g., a molding compound). As explained above, the frame 10 can be optically opaque. Therefore, the frame 10 between the first and second substrate sections 16a, 16b can help reduce crosstalk between the sensor die 24 and the emitter die 30. In such embodiments, the substrate 16 as seen from the front side 12 of the package can have the substrate sections 16a, 16b spaced apart by the frame 10, unlike the substrate 16 shown in FIG. 5.

The sensor package 1, in the illustrated embodiments, has only one sensor die 24. However, the sensor package 1 may have more than one sensor dies 24. The sensor die 24 has four bond pads on the back surface 27 for the wires 36 to be connected. However, the sensor die 34 can have any suitable number of bond pads.

There are two emitter dies 30 illustrated in FIGS. 7, 8, and 10. However, the package 1 may have any number of the emitter dies 30 suitable. In some embodiments, different emitter dies 30 in the substrate 16 can emit the same or different ranges of wavelengths. In some embodiments, each of the emitter dies 30 can comprise a light emitting diode (LED). Each of the emitter dies 30 as illustrated includes two bonding pads for the wires 38 to be connected. However, the emitter die 30 can have any suitable number of bond pads.

Similar to the electrical interconnects 28 through the TMVs 29 on the sensor die 24 illustrated with respect to, for example, FIG. 3, the integrated device die 34 can have the electrical interconnect 28 through the TMVs 29 to electrically connect the device die 34 to the external device.

Referring to FIG. 5, the package 1 has a package length L, a package width W, and a package height H, as similarly shown in FIG. 1. The area that is defined by the package length L and the package width W of the package 1 illustrated in FIG. 5 can be, for example, in a range of 0.2 mm$^2$ to 4 cm$^2$, in a range of 2 mm$^2$ to 2 cm$^2$, in a range of 40 mm$^2$ to 80 mm$^2$, or in a range of 50 mm$^2$ to 70 mm$^2$. The package height H of the package 1 shown in FIG. 5 can be, for example, in a range of 0.5 mm to 1.2 mm, or in a range of 0.7 mm to 1 mm.

Embodiments of the package 1 that includes the sensor die 24, the emitter dies 30, and the integrated device die 34, as opposed to having a sensor package, an emitter package, and an integrated device package separately, may reduce overall size of a system that utilizes the three components because the components can be closely disposed to one another and/or connected by the wires 36, 38 instead of external connections.

FIGS. 11 and 12 show cross-sectional views of the sensor die 24 attached to the substrate 16 in other embodiments. It should be understood that the sensor die 24 shown in FIGS. 11 and 12 can instead be an emitter die 30, in some embodiments. As shown here, the substrate 16 can have different shapes to provide optical advantages and/or to have physical properties to fit in the external devices. The optical advantages can include, for example, filtering, diffusing, splitting and/or polarizing the incident light. In some embodiments, for example, a first layer 16a directly below (closer to the first side 18) the sensor die 24 can comprise an optical filter, a second layer 16b below the first layer 16a can comprise a diffuser, a third layer 16c below the second layer 16b can comprise a waveguide, and a fourth layer 16d below the third layer 16c can comprise a polarizer film. Beneficially, the shape and multi-layer construction of the substrate 16 of FIGS. 11-12 can provide additional functionality, for, e.g., lensing, filtering, diffusing, splitting, diffracting and/or polarizing received light (in the case of a sensor die) and/or transmitted light (in the case of an emitter die). However, in some embodiments, the shape of the substrate 16 may be chosen for other design purposes.

Figure 13:
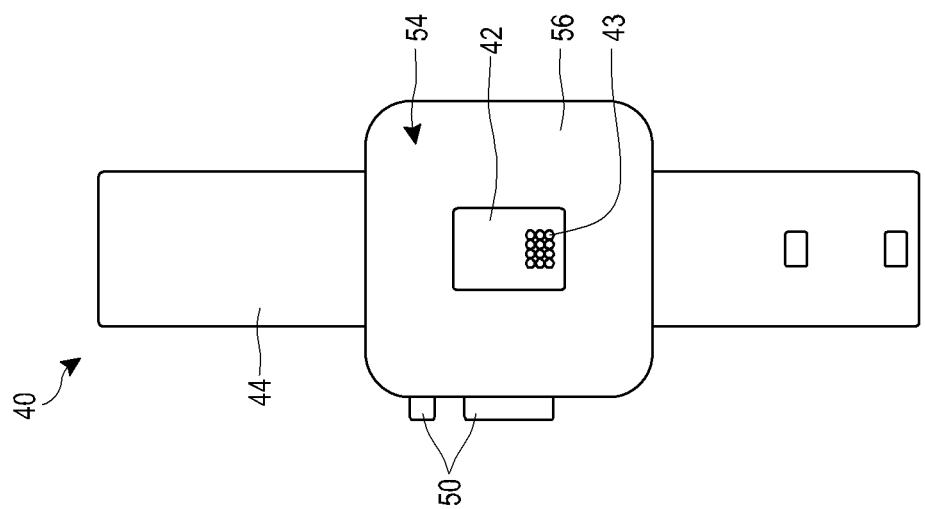
FIG. 13 is a schematic rear plan view of a wristband device that can incorporate the sensor packages disclosed herein, according to some embodiments.
Figure 14:
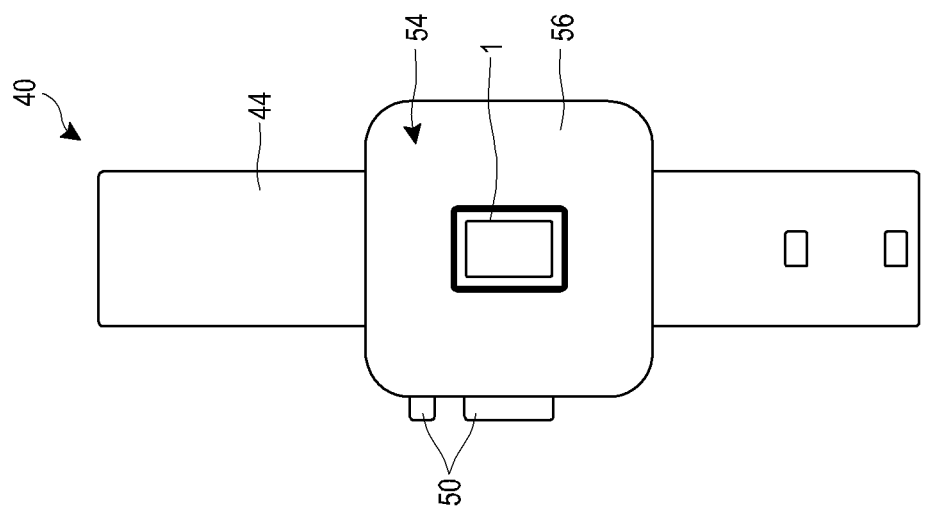
FIG. 14 is a schematic rear view of the wristband device of FIG. 13 having a sensor package.
Figure 15:
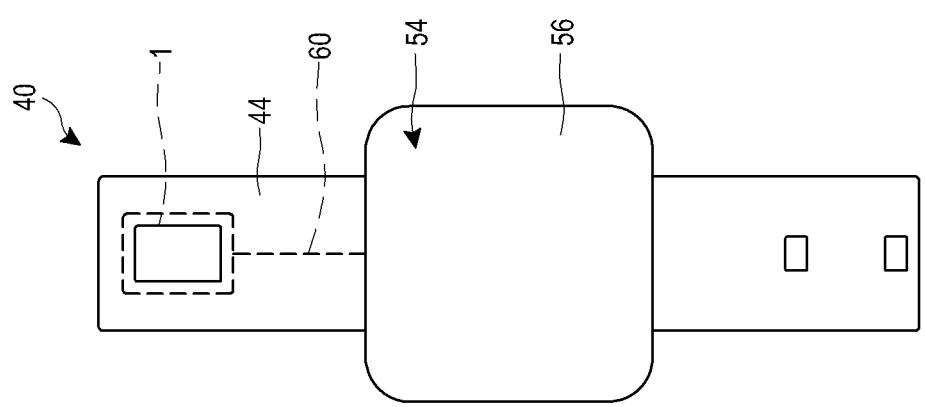
FIG. 15 is a schematic rear view of a wristband device having a sensor package in a band.
Figure 16:
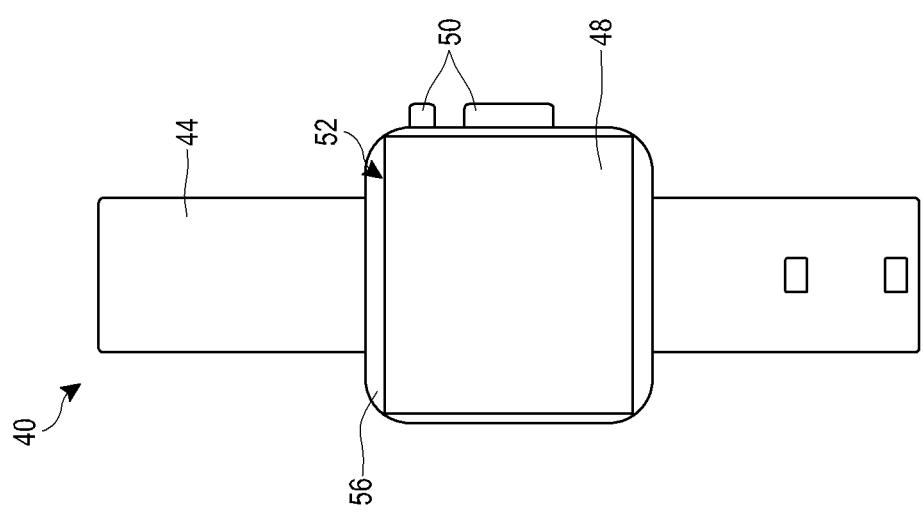
FIG. 16 is a schematic front plan view of the wristband device of FIGS. 13-14.
Figure 17:
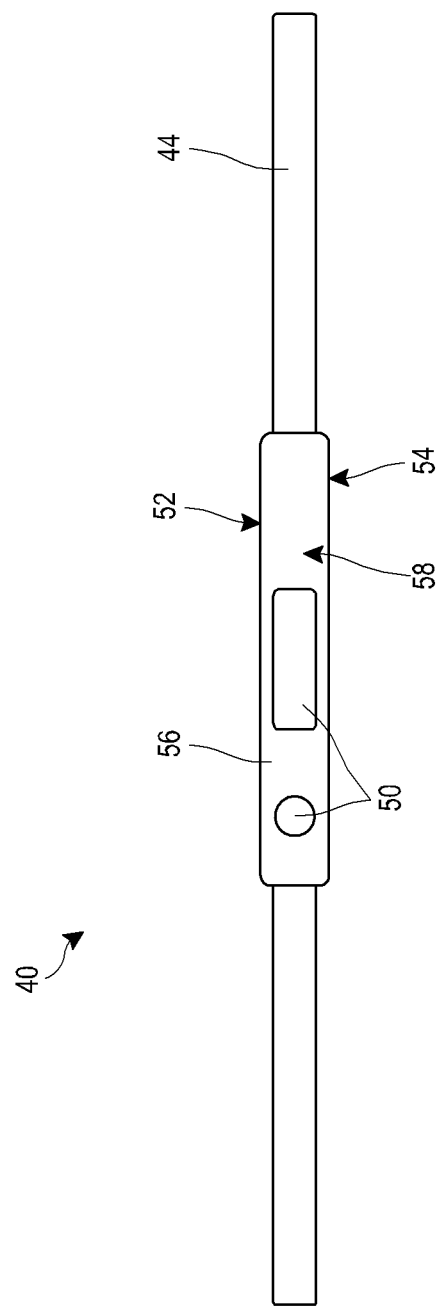
FIG. 17 is a schematic side elevational view of the wristband device of FIGS. 13-14.

FIGS. 13-14 show an example of the external device in a form of a wristband device 40 that the sensor package 1 can be integrated with or coupled to. FIGS. 13 and 14 are rear views showing a rear side 54 of an embodiment of the wristband device 40 without the package 1 (FIG. 13) and with the package 1 (FIG. 14). FIG. 15 is a rear view of another embodiment of the wristband device 40. FIG. 16 is a front view showing a front side 52 of the wristband device 40. FIG. 17 shows a side elevational view of the wristband device 40. The wristband device includes a band 44 and a body 56. The wristband device 40 can be worn on a user by fastening the band 44 around the user's wrist. In some embodiments, the wristband device 40 can be used as a heart rate monitoring system. In such embodiments, the body 56 of the device 40 can include, for example, a slot 42 (FIG. 13) for receiving the package 1 for measuring the heart rate, a user interface 48 (FIG. 16), and user controls 50.

In the embodiment of FIGS. 13-14, the package 1 can be physically and electrically connected to the device 40 at the slot 42 via the contacts 43. For example, the interconnects 28 can be electrically connected to the contacts 43 of the device 40, e.g., by soldering or other conductive connection. In some embodiments, the package 1 can be connected to the body 56 by soldering in a manufacturing process. However, it should be understood that the package 1 can be attached to the body 56 in any manner suitable. In some embodiments, the package 1 may be removable. In such embodiments, the interconnects 28 and/or the contacts 43 can comprise a compression fitting connector and/or a pogo pins. In the embodiment of FIG. 15, the package 1 can be disposed in the band 44 of the device 40 and the package 1 can be electrically connected with the body of the device 40 via an electrical interconnect 60. The interconnect 60 can comprise, for example, a trace embedded in the band 44. In some embodiments, the package 1 can be removable from the band 44.

In some embodiments, the body 56 include a battery for supplying electricity to the package 1. In some embodiments, the band 44 can include a flexible battery. In some embodiments, there can be a solar panel on the front side 52 to charge the battery. Electrical connection between the battery and the package 1 may be embedded in the band 44 and/or the body 56.

Referring to FIG. 16, in some embodiments, the user interface 48 can comprise a display. The display can have a touch sensor function where the user can touch the display to control the device 40. The user interface 48 can display the heart rate of the user. In some embodiments, the user interface can be eliminated from the body 56 and an external device, such as a smart phone, a laptop or any external display that can be used as the user interface 48.

Referring to FIG. 17, the body 56 can have the user controls 50 on a side wall 58 between the front side 52 and the rear side 54. In some embodiments, the user controls 50 can comprise a port that can be used to connect the device 40 to external systems (e.g., a computer, electric outlets, earbuds, etc.) via a cable and/or a cord. In some embodiments, the device 40 can be wirelessly connected to external systems without the controls 50, for example via Wi-Fi or the Bluetooth. FIG. 17 shows two user controls 50 with circular shape and rectangular shape. However, there can be any number of user controls 50 with any shape suitable for the purported usage. In some embodiments, the user controls 50 may be used for charging a battery embedded in the device 40 when the device 40 is connected with the external system. However, the device 40 can comprise a designated charging port separate from the user controls 50.

In some embodiments, the wristband device 40 may further include electrode pads for measuring a heart rate independent of the package 1 for a better accuracy than solely using the package 1 as a heart rate monitoring system.

Although this invention has been disclosed in the context of certain embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. An optical device package comprising:
a substrate that passes light at an optical wavelength, the substrate having a first side, a second side opposite the first side and a side wall extending between the first and second sides;
an optical device assembly mounted to the second side of the substrate, the optical device assembly comprising an integrated device die, the integrated device die having a first surface mounted to and facing the substrate and a second surface opposite the first surface; and
a molding compound disposed at least partially over the second surface of the integrated device die and at least partially along a side wall of the substrate.

2. The optical device package of claim 1, wherein the substrate comprises glass.

3. The optical device package of claim 1, wherein the integrated device die comprises a sensor die.

4. The optical device package of claim 3, wherein the sensor die comprises an active surface facing the substrate.

5. The optical device package of claim 1, wherein the second surface has one or more electrical contacts configured to electrically connect the integrated device die to an external device through the molding compound.

6. The optical device package of claim 5, further comprising one or more through mold vias (TMVs) that extend from the one or more electrical contacts through the molding compound, the TMVs configured to receive electrical interconnects, the electrical interconnects electrically connect the optical device assembly to the external device.

7. The optical device package of claim 1, wherein the substrate comprises one or more of a filter, a diffuser, a polarizer, and a waveguide or beam steering element.

8. The optical device package of claim 1, wherein the substrate comprises a first portion for mounting the integrated device die and a second portion for mounting a second integrated device die of the optical device assembly.

9. The optical device package of claim 8, wherein the first portion and second portion of the substrate are spaced apart by the molding compound.

10. The optical device package of claim 1, wherein the molding compound disposed around side edges of the integrated device die.

11. An optical device package comprising:
a substrate that passes light at an optical wavelength, the substrate having a first side, a second side opposite the first side and a side wall extending between the first and second sides;
an optical device die having a first surface mounted to the second side of the substrate, the optical device die configured to transmit or detect light through the substrate at the optical wavelength;

a processor die mounted to the second side of the substrate, the processor die electrically connected to the optical device die; and a frame disposed at least partially along the side wall of the substrate.

12. The optical device package of claim 11, wherein the optical device die comprises an optical emitter die configured to emit light through the substrate.

13. The optical device package of claim 11, wherein the optical device die comprises an optical sensor die configured to detect light that has passed through the substrate at the optical wavelength.

14. The optical device package of claim 11, further comprising a second optical device die.

15. The optical device package of claim 14, wherein the optical device die and the second optical device die comprise an optical emitter die and an optical sensor die respectively, wherein the optical emitter die is configured to emit light through the substrate and the optical sensor die configured to detect light that has passed through the substrate at the optical wavelength.

16. The optical device package of claim 11, wherein the processor die receives signals from or transmits signals to the optical device die.

17. An optical device package comprising:

a substrate that passes light at an optical wavelength, the substrate having a first side, a second side opposite the first side and a side wall extending between the first and second sides;

an optical device die having a first surface mounted to and facing the second side of the substrate, the optical device die configured to transmit or detect light through the substrate; and a frame disposed at least partially around the side wall and at least partially over a back side of the optical device die, the frame being opaque to at least the optical wavelength.

18. The optical device package of claim 17, wherein the optical device die comprises a sensor die.

19. The optical device package of claim 17, wherein a height between the first side of the substrate and the back side of the optical device die is in a range of 0.5 mm to 1.2 mm.

20. The optical device package of claim 17, wherein the frame comprises molding compound.

* * * * *